(12) United States Patent
Gregory et al.

(10) Patent No.: US 6,290,668 B1
(45) Date of Patent: Sep. 18, 2001

(54) LIGHT DELIVERY CATHETER AND METHODS FOR THE USE THEREOF

(76) Inventors: Kenton W. Gregory, 3969 SW. Wapato Ave., Portland, OR (US) 97201; Christopher H. Porter, 19576 NE. 127th Pl., Woodenville, WA (US) 98072; Mark Anders Rydell, 516 Turnpike Rd., GoldenValley, MN (US) 55416; Robert Ziebol, 13041 Jefferson St., Blaine, MN (US) 55434

( * ) Notice: Subject to any disclaimer, the term of this patent is extended or adjusted under 35 U.S.C. 154(b) by 0 days.

(21) Appl. No.: 09/070,634

(22) Filed: Apr. 30, 1998

(Under 37 CFR 1.47)

(51) Int. Cl.[7] .......................... A61B 17/20; A61M 31/00; A61M 25/00
(52) U.S. Cl. ............................. 604/22; 604/510; 604/523
(58) Field of Search .................. 604/21, 22, 43, 604/507, 508, 510, 518, 247, 523, 528, 539; 606/7, 15, 12; 607/89; 128/898

(56) References Cited

U.S. PATENT DOCUMENTS

| | | | |
|---|---|---|---|
| 3,582,187 | 6/1971 | Skillman | 350/179 |
| 3,725,810 | 4/1973 | Ashkin et al. | 331/94.5 |
| 3,920,980 | 11/1975 | Nath | 240/1 |
| 4,045,119 | 8/1977 | Eastgate | 350/96 |
| 4,669,465 * | 6/1987 | Moore et al. | 128/303.1 |
| 4,729,621 | 3/1988 | Edelman | 350/96.15 |
| 4,754,328 | 6/1988 | Barath et al. | 358/98 |
| 4,768,858 | 9/1988 | Hussein | 350/96.32 |
| 4,784,132 | 11/1988 | Fox et al. | |
| 4,800,876 | 1/1989 | Fox et al. | |
| 4,830,460 | 5/1989 | Goldenberg | 350/96.26 |
| 4,832,444 | 5/1989 | Takahashi et al. | 350/96.26 |
| 4,838,269 * | 6/1989 | Robinson et al. | 128/344 |
| 4,842,390 | 6/1989 | Sottini et al. | 350/96.15 |
| 4,848,336 | 7/1989 | Fox et al | |
| 4,848,893 | 7/1989 | Chin | 604/21 |
| 4,913,505 | 4/1990 | Levy | 350/96.1 |
| 5,002,559 | 3/1991 | Tower | 606/194 |
| 5,005,944 | 4/1991 | Laakmann et al. | 350/96.32 |
| 5,083,549 | 1/1992 | Cho et al. | 128/7 |
| 5,167,623 | 12/1992 | Cianci et al. | 604/43 |
| 5,169,396 | 12/1992 | Dowlatshahi et al. | 606/15 |
| 5,203,338 | 4/1993 | Jang | 128/662.06 |
| 5,219,335 | 6/1993 | Willard et al. | 604/164 |
| 5,221,255 | 6/1993 | Mahurkar et al. | 604/43 |
| 5,292,305 | 3/1994 | Boudewijn et al. | 604/43 |
| 5,314,408 | 5/1994 | Salmon et al. | 604/22 |
| 5,327,885 | 7/1994 | Griffith | 128/662.06 |
| 5,400,789 | 3/1995 | Griffith | 128/662.06 |
| 5,458,584 | 10/1995 | Ginn et al. | 604/280 |
| 5,498,236 | 3/1996 | Dubrul et al. | 604/22 |
| 5,531,700 | 7/1996 | Moore et al. | 604/164 |
| 5,571,151 | 11/1996 | Gregory | 607/88 |
| 5,620,417 | 4/1997 | Jang et al. | 604/96 |
| 5,709,676 | 1/1998 | Alt | 606/7 |
| 5,728,067 | 3/1998 | Enger | 604/102 |
| 6,022,309 * | 2/2000 | Celliers et al. | 600/7 |

FOREIGN PATENT DOCUMENTS

WO 95/07720 * 3/1995 (WO).

* cited by examiner

Primary Examiner—Richard K. Seidel
Assistant Examiner—Michael J. Hayes

(57) ABSTRACT

This invention provides a light delivery catheter having a proximal shaft with two lumens and a distal shaft connected to the proximal shaft, which distal shaft has only a single lumen. A guidewire and a light guide are received in the first and second lumens resectively, of the proximal shaft, either of which may be extended into the single lumen of the distal shaft, the distal shaft being sufficiently flexible to facilitate movement of the catheter through tortuous paths. A hub is provided having ports through which appropriate fluids may be applied to the lumens. When used to remove a blood clot in a blood vessel of the brain or other part of the body, the guidewire is extended through the single lumen in the distal shaft and is utilized to guide the catheter adjacent the clot, at least one guidewire/light guide exchange being performed to ablate the clot. Alternatively, the catheter may initially be passed through the clot to the distal side thereof and the catheter retracted through the clot as light energy and contrast fluid are applied therethrough.

9 Claims, 3 Drawing Sheets

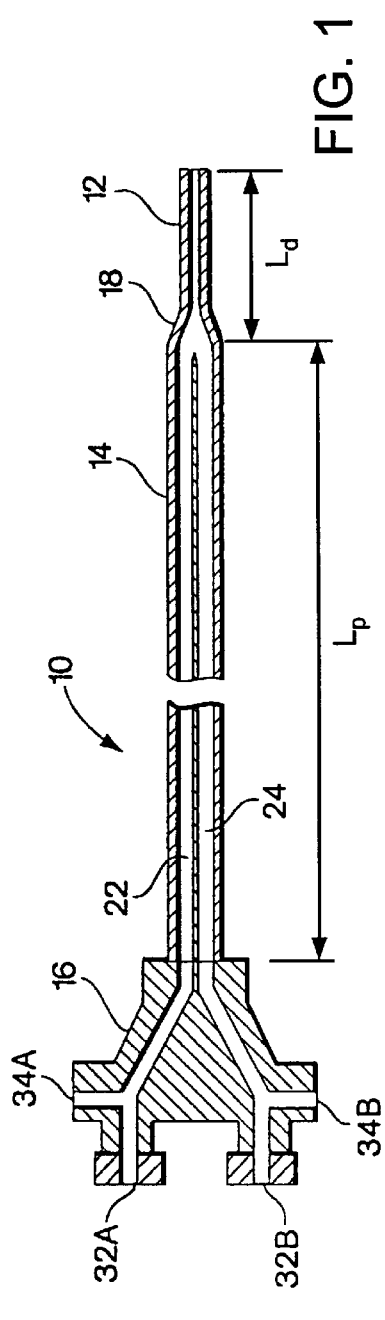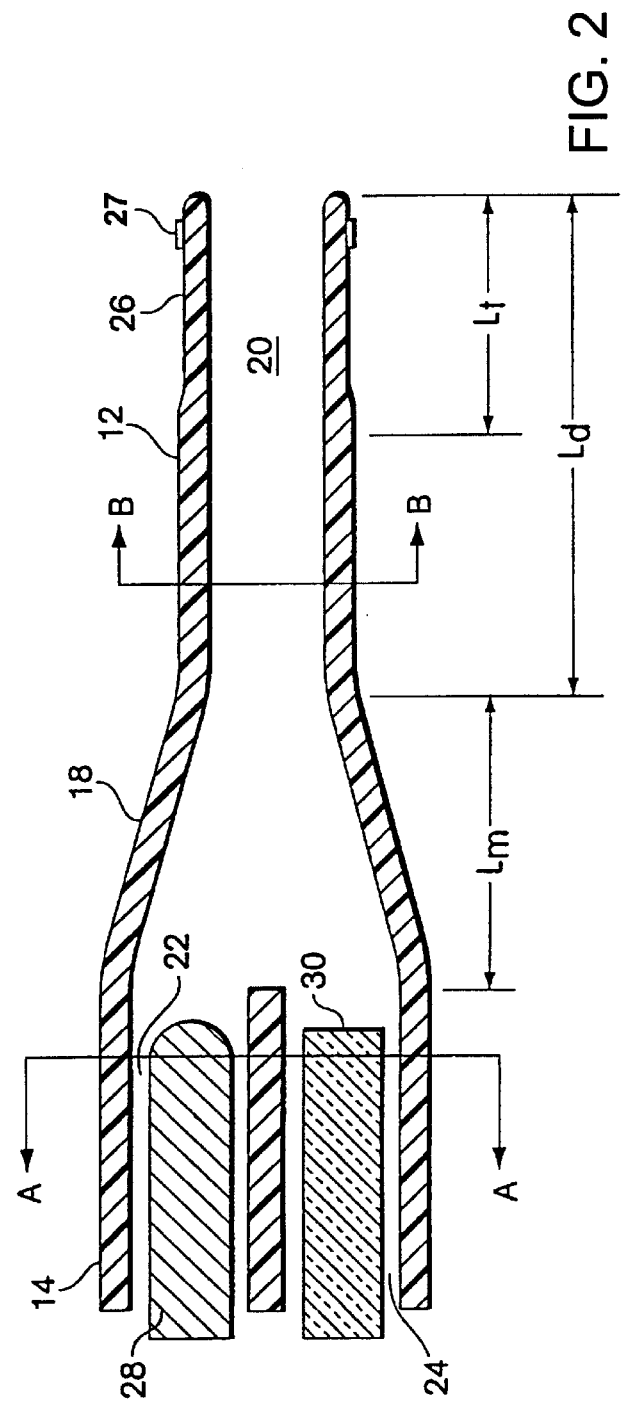

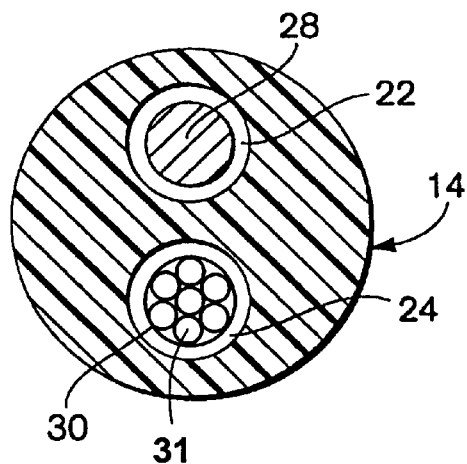
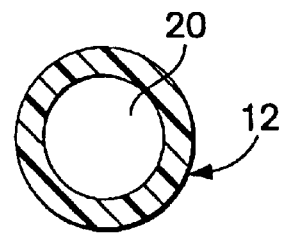
FIG. 3A        FIG. 3B
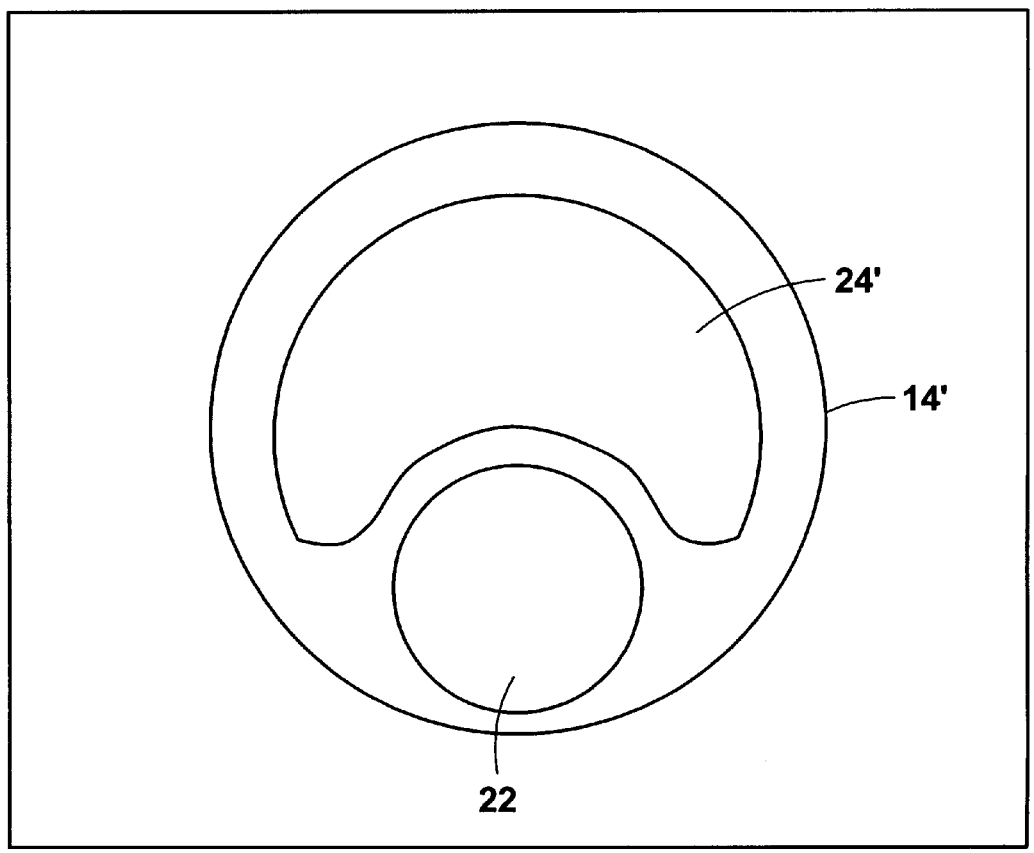
FIG. 3A'

LIGHT DELIVERY CATHETER AND METHODS FOR THE USE THEREOF

This application claims the benefit of U.S. application Ser. No. 08/846426 filed Apr. 30, 1997 and converted to U.S. Provisional Application filed on Apr. 8, 1998.

FIELD OF THE INVENTION

This invention relates to light delivery catheters and more particularly to both a light delivery catheter, which may be utilized as a fluid flow catheter, and which permits the rapid exchange of a guidewire and a light guide at the distal end thereof while both components remain in the catheter, and to methods for utilizing such catheter or others for removing a blood clot in a blood vessel, for example, a blood vessel in the brain.

BACKGROUND OF THE INVENTION

Blood clots in cerebral arteries and other vessels of the brain can cause strokes and other neurological problems. It is therefore desirable that these blood clots be broken up and removed. One technique which has been utilized to accomplish this objective in the past is laser ablation. However, because of the tortuous nature of the brain vessels and the vessels leading thereto, moving a catheter into a position to deliver light energy to a clot requires that the catheter, or at least the distal portion thereof, be very flexible, and normally requires that the catheter be advanced over a guidewire to a desired location. However, a light delivery catheter also normally requires a light guide passing through the catheter. But, a catheter having two lumens passing therethrough, one for a guidewire and one for a light guide, would be too stiff, particularly at the distal end thereof, to traverse the tortuous path to the brain; therefore catheters used for ablation of brain clots have heretofore utilized a single lumen, with the guidewire being removed when the catheter is positioned adjacent a clot and a light guide then inserted through the catheter to a position adjacent the clot.

However, in order to avoid damaging parts of the vessel other than the clot, or even puncturing the vessel, relatively low energy is used for such procedures, so that the first delivery of light energy to the clot normally does not result in ablation thereof. In order for the procedure to be most effective, it is desirable that the catheter be repositioned adjacent to the new leading edge of the clot before light energy is again provided. However, it is also preferable that the guidewire be utilized for such repositioning. Therefore, with current equipment, the doctor performing the procedure has had three choices, namely (a) attempt to reposition the catheter without the use of a guidewire; (b) not reposition the catheter and continue ablation from the catheter's original position; or (c) remove the light guide through what may be as much as 150 centimeters (approximately 5 feet) of catheter, reinsert a guidewire to reposition the catheter, and then remove the guidewire and reinsert the light guide. The first procedure is difficult to perform, the second results in reduced energy being transmitted to the clot for subsequent applications of light energy and, because of the tortuous nature of the vessel, may result in light being directed at a portion of the vessel other than the clot, resulting in reduced clot ablation. The third procedure is tedious and time-consuming. Therefore, existing light delivery catheters for laser thrombosis or ablation of blood clots impose limitations on the doctors performing such procedures and result in less than optimum procedures being utilized. The same problems arise where the laser is only used to cavitate the clot and a clot-busting drug such as tPA is used in conjunction with ablation/cavitation to assist in breaking up the clot. This procedure also requires in most instances several iterations of light energy and drug application before the blood clot is fully broken up.

Another potential problem in using a light delivery catheter to remove a blood clot in the brain is that vessel walls in the brain are relatively thin and subject to perforation, particularly by a catheter being pressed there against. This risk is reduced by having a very flexible guidewire being used to lead the catheter through the vessel and by not having an unguided catheter moving forward through the vessel.

Still another potential problem is that, since the blockage at a clot prevents any emboli created during the lysing or ablation process from being washed downstream, such emboli therefore must travel retrograde or upstream to areas of the brain which are unaffected by the clot. These emboli or particles traveling through vessels which may already be narrowed by the presence of the catheter therein can, in a worse case scenario, result in a stoke in such unaffected areas of the brain. It would therefore be preferable if such emboli could be washed or flushed downstream through vessels in area of the brain already affected by the stoke and through vessels not partially blocked by a catheter so as to both reduce the likelihood of a further small stroke and to minimize any new damage caused thereby.

Finally, all of the current procedures for the ablation of blood clots in the brain are relatively time consuming. Since the longer the procedure, the harder it is on both the physician and patient, and the more expensive the procedure becomes, it is desirable that any procedure utilized be as efficient as possible so as to minimize the time required for its performance.

Similar problems may exist when using a light-delivery catheter to remove clots from blood vessels in parts of the body other than the brain. A need therefore exists for an improved light delivery catheter which permits the catheter to be sufficiently flexible, at least in the distal portion thereof, to advance through tortuous brain or other vessels with minimum risk of damage thereto while still permitting rapid exchange between guidewire and light guide so as to facilitate rapid and accurate repositioning of the catheter adjacent the current leading edge of the clot between each delivery of light energy. It is also desirable that the catheter used operate in a fluid flow mode, facilitating the delivery of light energy to the clot and that the procedure used facilitate washing of emboli creating by the ablation process downstream so as to minimize risk of secondary stroke, particularly in unaffected areas of the brain.

SUMMARY OF THE INVENTION

In accordance with the above, this invention provides a light delivery catheter which has a proximal shaft with first and second lumens extending therethrough, a distal shaft having a single lumen extending therethrough and a short tapered section interconnecting the proximal and distal shafts. The first and second lumens are adapted to receive a guidewire and a light guide, respectively, with the single lumen being aligned with the first and second lumens to permit either the guidewire in the first lumen or the light guide in the second lumen to extend into the single lumen in the distal shaft. The distal shaft is flexible and preferably has a distal portion, which may be approximately 1 to 2 centimeters long, which is tapered to enhance flexibility. The entire distal shaft may be approximately 20 to 30 centimeters long. A port may be provided at the proximal end of the proximal shaft through which contrast fluid may be applied to flow through the second lumen and out through the single lumen. The distal shaft is preferably formed of a material having a refractive index which is less than that of such contrast fluid, which material is a floropolymer for preferred embodiments. Both the proximal and distal shaft may be formed of such floropolymer material. Particularly where the catheter is being used with contrast fluid flowing therethrough, the second lumen may be larger than the first lumen. A marker band of a radiopaque material may also be applied at the distal end of the distal shaft.

For preferred embodiments, a light guide is provided in the second lumen and a guidewire in the first lumen of the proximal shaft. A hub is also provided at the proximal end of the proximal shaft, which hub has at least three ports. A first port is connected to the first lumen through which a guidewire may enter the lumen and a second port is connected to the second lumen through which a light guide may enter the second lumen. A third port is connected to one of the lumens through which a fluid may be applied to the lumen. For preferred embodiments, there are four ports, with a third port being connected to apply fluid to the first lumen and a fourth port being connected to the second lumen through which a contrast fluid may be applied to the lumen. The first and second ports may be hemostatic valves and the third and fourth ports may be Leur connectors. A check valve may be provided on each of the Leur connectors.

The invention also includes a method for removing a blood clot in a blood vessel, for example a blood vessel in the brain, which method may utilize a light delivery catheter of the type described above. The method includes the steps of: (a) advancing the guidewire extending through the single lumen and out a short distance from the distal end of the catheter, and the catheter mounted thereon to the clot; (b) retracting the guidewire from the single lumen so that it is fully within the first lumen and advancing the light guide into the single lumen to a point near the distal end thereof; and (c) applying laser light energy through the light guide to the clot.

For preferred embodiments, the method also includes the step performed before and during step (c) of (d) flowing a contrast fluid through the second lumen and the single lumen to the clot, light being guided to the clot from the end of the light guide through the contrast fluid. The method preferably also includes the steps performed after step (c) of (e) retracting the light guide from the single lumen so that it is fully within the second lumen and advancing the guidewire through the single lumen to extend from the distal end thereof; (f) using the guidewire to reposition the catheter relative to the clot; and (g) repeating steps (b), (c) and (d). There may be several iterations of steps (e), (f) and (g). Finally, the method may include the step performed during or after each performance of step (c) of terminating step (d), the flowing of contrast fluid, and flowing a clot-bursting drug through one of the first and second lumens, preferably the first lumen, and the single lumen to the clot.

Alternatively, rather than stopping at the clot during step (c) as indicated above, the guidewire and catheter may be advanced through the clot to the distal side thereof. When light energy is applied to the light guide, the catheter may then be slowly pulled back through the clot as the clot is lysed. For this embodiment of the method, the flowing contrast fluid flows through the clot. Acoustic feedback and/or optical feedback may be provided as to the lysing of the clot and this feedback may be utilized either by a physician or other person performing the procedure or automatically to control the rate at which the catheter is pulled back through the clot. If a single pass of the catheter through the clot does not result in a sufficient ablation or lysing thereof, the steps of passing the catheter through the clot and pulling the catheter back through the clot as light energy is being applied therefrom may be repeated. This procedure may be performed with a catheter of the type described earlier, or may be performed using for example a standard single-lumen catheter.

The foregoing and other objects, features and advantages of the invention will be apparent from the following more particular description of a preferred embodiment of the invention as illustrated in the accompanying drawings.

IN THE DRAWINGS

FIG. 1 is a sectional view of a catheter in accordance with a preferred embodiment of the invention.

FIG. 2 is an enlarged sectional view, not to scale, of a distal portion of the catheter shown in FIG. 1 illustrating the positioning of a guidewire and a light guide in lumens of the catheters proximal shaft.

FIG. 3A is a sectional view of the proximal shaft taken along the line A—A in FIG. 2.

Figure 4:
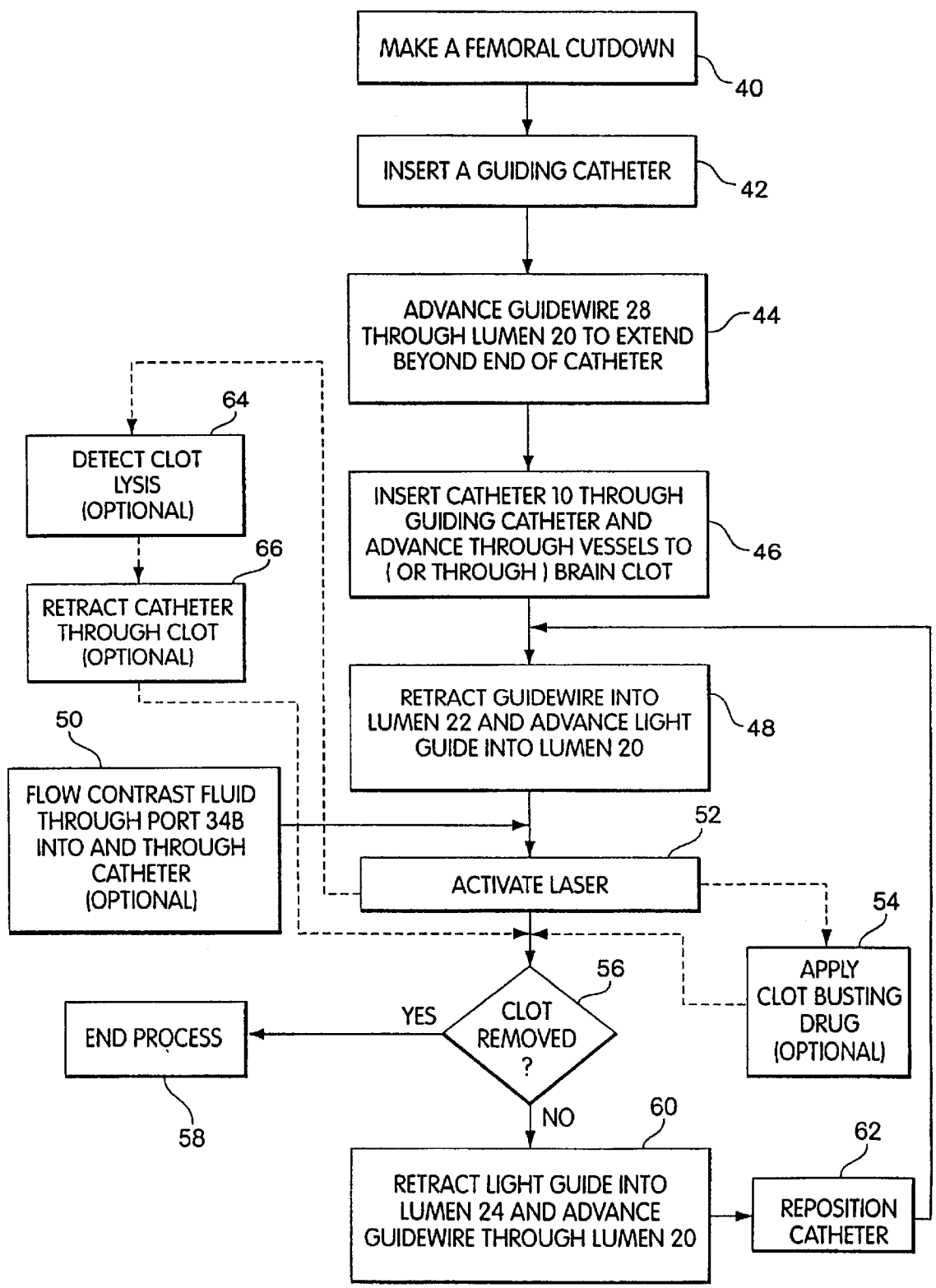

FIG. 3A' is a sectional view of the proximal shaft taken along the line A—A in FIG. 2 for an alternative embodiment of the invention.

FIG. 3B is a sectional view of the distal shaft taken along the line B—B in FIG. 2

FIG. 4 is a flow diagram of a process for utilizing the catheter of FIGS. 1–3 to remove a clot, including variations thereon.

DETAILED DESCRIPTION

Referring to FIG. 1, the catheter 10 in accordance with the teachings of this invention has a distal shaft 12, a proximal shaft 14 and a hub 16, the distal shaft and proximal shaft being interconnected through a short transition region 18. Distal shaft 12 has a single lumen 20 while proximal shaft 14 has a first lumen 22 and a second lumen 24.

The distal end 26 of distal shaft 12 is tapered to enhance flexibility and a marker band 27 of a radiopaque material is provided on the distal end of distal shaft 12. Marker band 27 facilitates visualization under fluoroscopy. For a preferred embodiment, the total length $L_d$ of the distal shaft is 20 to 30 centimeters, with the length $L_t$ of the tapered portion 26 being approximately 1 to 2 centimeters. The width of marker band 27 might for example be 0.5 mm. For an illustrative embodiment, the outer diameter of the main portion of the distal shaft is less than 3 french (1 mm) and tapers to approximately 2.5 french (0.8 mm) in tapered region 26. The diameter of lumen 20 is approximately 0.036 inches (0.9 mm) and tapers to approximately 0.032 inches (0.8 mm) in distal region 26. Particularly where catheter 10 is to be utilized as a fluid flow catheter, distal shaft 12 should be formed of a material having a refractive index which is less than that of the contrast fluid being utilized, certain floropolymer materials being suitable for such use.

The proximal shaft will have a length sufficient to permit the catheter to reach from the region where a cut is made to the region where a blood clot is to be removed. For an application where the catheter is to extend from a femoral cut to a blood clot in the brain, the length of the proximal shaft might for example be 130 cm. The overall diameter of the proximal shaft might be approximately 0.052 inches (1.3 mm) where the catheter is being used for laser brain ablation. Where the catheter is being used as a fluid flow catheter with contrast fluid flowing through lumen 24, this lumen should be slightly larger than lumen 22; for example, 0.016 inches in diameter for lumen 22 and 0.025 inches for lumen 24. An alternative proximal shaft is shown in FIG. 3A' which maximizes the area in lumen 24 for better fluid flow. As shown in the Figures, a flexible guidewire 28 may be positioned in lumen 22 and a multi-fiber light guide 30 may be positioned in lumen 24. Light guide 30 for a preferred embodiment is formed of seven small-diameter fibers 31 (FIG. 3A) each of which may be 60 microns, rather than a single large fiber to achieve the flexibility necessary for traversing the tortuous path to and through the brain while still being capable of transmitting large pulses of light energy. Other fiber optic bundles might be employed in suitable applications.

The distal shaft 12 and proximal shaft 14 are connected in a tapered transition region 18 having a relatively short length $L_m$ which for an illustrative embodiment, is approximately 2.5 cm. The tapered region may be manufactured by reflowing a single lumen tube, having a diameter similar to the proximal shaft, under heat and pressure such that it tapers down to a diameter similar to the distal shaft. The attachment may be accomplished by reflowing the floropolymers under heat and pressure or by solvent bonding, with either of these techniques being performed utilizing techniques known in the art. The attachment is done such that each of the lumens in the proximal shaft is aligned with and connected to the lumen 20 in distal shaft 12. During the attachment process, the lumens are kept open by using mandrels inside the lumens which prevent the lumens from collapsing.

Hub 16 has four ports, two of which ports 32A, 32B are hemostatic openings or valves and two of which ports 34A and 34B are Leur ports which may contain female Leur connectors. Ports 32A and 34A are connected to lumen 22 and ports 32B and 34B are connected to lumen 24. Devices such as guidewire 28 and light guide 30 may be passed into the appropriate lumen through the corresponding hemostatic valve 32 and an appropriate fluid may be flowed or flushed through a lumen 22,24 through the corresponding Leur port 34. For a preferred embodiment, a contrast fluid may be flowed through port 34B into lumen 24 and a saline solution or, for some embodiments, a clot-busting drug such as tPA, may enter and flow through port 34A and lumen 22. Leur ports 34 preferably have check valves to prevent fluid from flushing back upstream through lumens 22 and 24.

In operation, catheter 10 may be utilized to remove a blood clot in the brain by following the procedure shown in FIG. 4. In particular, the procedure is initiated by making a cut-down into for example an artery at an appropriate place in the anatomy, for example a femoral cut-down (step 40). A guiding catheter is then inserted through the cut-down (step 42) and extended for a selected distance on the path to the brain. Guidewire 28 is then advanced through lumen 20 to protrude approximately 3 centimeters beyond the distal end of catheter 10 (step 44) and the catheter is then inserted into the guiding catheter and advanced through the tortuous path into the cerebral arteries or other vessels to the clot (step 46). This is done in substantially the same way as a standard microcatheter is advanced. For an alternative embodiment of the method discussed hereinafter, the guidewire and catheter are advanced through the clot to the distal side thereof. The clot is generally soft enough so that the guidewire and catheter may be advanced therethrough without exerting undo force so as to risk damage to a vessel wall. If the catheter cannot easily be advanced through the clot, low energy light pulses may be applied to the clot to permit the catheter to be fully advance therethrough. Such light energy assisted passage through the clot should normally not be required.

Once the catheter is in position adjacent the clot, guidewire 28 is retracted fully into lumen 22 and light guide 30 is advanced into position in lumen 20 a short distance (a few centimeters) from the distal end thereof (step 48). Radiopaque markers on the light guide 30 (not shown) and marker 27 may be utilized as references in properly positioning the light guide. For preferred embodiments, either before or after step 48, a power injector is used to inject contrast fluid through port 34B and through lumen 24 and lumen 20 to the clot (step 50). As is known in the art, and as is taught in U.S. Pat. No. 5,304,171 issued Apr. 19, 1994, entitled "Catheter Devices and Methods for Delivery," such fluid facilitates the transmission of light from the light guide to the clot to be ablated. Either from step 50, or from step 48 if step 50 is not performed, the operation proceeds to step 52 during which a laser is activated, for example by having a doctor operate a foot switch, to cause selected pulsed light energy to be applied through light guide 30, which is now positioned adjacent the distal end of catheter 10, and thus to the clot, and through the contrast fluid (or blood if flowing contrast fluid is not used), to the clot to cause ablation thereof. Typically, the energy applied is not sufficient at this point to fully remove the entire clot. For some embodiments of the invention, the laser blast is used to cavitate and agitate the clot, providing a larger surface area and weakening the clot bonds for a clot-busting drug such as tPA which may be applied for example through port 34A and lumens 22 and 20 to the clot to effect removal of the clot (step 54). The cavitation also drives the clot-busting drug into the clot.

From step 54, if performed, or from step 52, the operation proceeds to step 56 to determine if the clot has been fully ablated. If during step 56, it is determined that the clot has been fully ablated, the operation proceeds to step 58 to terminate the procedure. However, if during step 56 it is determined that the clot has not been fully removed, the operation proceeds to step 60 during which the light guide 30 is retracted into its lumen 24 in distal shaft 14 and guidewire 28 is again advanced through lumen 20 and slightly beyond the distal end thereof The operation then proceeds to step 62 to reposition the catheter adjacent the leading edge of the clot. When step 62 has been completed, the operation returns to step 48 to again bring light guide 30 adjacent the distal end of catheter 10. Steps 48-62 are then repeated until, during a step 58, it is determined that the clot has been fully removed so that the operation may be terminated.

If during step 46 the catheter is advance through the clot, then, once the laser is activated during step 52, the operation proceeds to steps 64 and 66 to detect lyses of the clot as the catheter is slowly retracted through the clot. More particularly, the contrast fluid facilitates visualization of the clot removal process so that, while the doctor is pulling back slowly on the catheter, the doctor may watch the progress of clot removal using fluoroscopy and use the fluoroscopic image to determine the optimal rate of pullback. The doctor may also use acoustic feedback, either in addition to or instead of the fluoroscopic feedback to held determine the rate of pullback. The acoustic feedback results in the fact that a "popping" noise is produced by the ablation process, the acoustic energy being a function of the ablation which is occurring. Thus, retraction may be performed when the acoustic energy level drops to a level indicating that little if any ablation is occurring at the current location of the catheter. Alternatively, the pullback of the catheter through the clot may be performed automatically with acoustic feedback from a microphone position to receive the acoustic energy being utilized to control the rate of catheter movement.

The pullback procedure is effective because the clot tends to close behind the catheter as the catheter is pulled back, permitting lysis on the clot to occur. Normally this procedure should result in a complete ablation, or at least a sufficient ablation of the clot during a single pass through the clot. However, if fluoroscopy shows that there is still a clot in the vessel, or at least sufficient material of the clot in the vessel so that further removal is desirable, the catheter may be advanced through the clot again, preferably with the use of a guidewire, and step 50, 52, 64 and 66 repeated to assure removal of the clot. Alternatively, if there is an opening through the clot, a repeating of only steps 50 and 52 with the catheter on the proximal side of the clot may be sufficient.

The procedure involving passing the catheter through the clot during step 46 and performing step 64 and 66 during steps 50 and 52 has a number of potential advantages. First, as indicated earlier, forward movement of the catheter without a guidewire risks puncture of the brain vessel. Such risk does not exist when the catheter is being pulled back through the clot. Therefore, unless time consuming exchanges between guidewire and lightpipe are being made a number of times during the ablation of the clot, advancing the catheter through the clot as ablation occurs poses a small potential danger of vessel damage. As indicated earlier, no such danger exists when a catheter is pulled back through the clot. Further, by permitting the ablation of the clot to occur without the need for wire/lightpipe exchanges, the ablation of a clot can be more quickly effected.

Another, and perhaps more significant advantage of this alternative procedure is that it permits emboli created during the ablation process to be washed downstream by the contrast fluid, and to some extent blood, flowing through the clot. In the worst case scenario, the emboli will result in a stroke in an area of the brain already affected by the stroke rather than in an unaffected area of the brain upstream from the clot.

Further, since this procedure does not normally require frequent guidewire/light guide exchanges, this procedure can also be advantageously performed using for example a standard single lumen catheter and such method is also within the contemplation of the invention. Any of the methods described may also be used in appropriate cases to ablate blood clots in blood vessels located in parts of a patient's body other than the brain.

While the invention has been particularly shown and described above with reference to is preferred embodiments, it is apparent that these embodiment are by way of example only for a particular application in removing brain clots, and that the dimensions, materials, and other characteristics of the catheter shafts, their interconnection and the devices passing through the lumens therein will vary with application. For example, in some cases, Nitroglycerin (vasodilator) may be injected through port 34A to reduce vasospasm. The catheter may also be used in other procedures requiring two devices to be used during the procedure, such as, for example, in photo dynamic therapy (PDT) which uses a light guide and a guidewire. Variations in the methods, over and above those indicated, are also possible. Thus, while the invention has been particularly shown and described above with reference to preferred embodiments, the foregoing and other changes in form and detail may be made therein by those skilled in the art without departing from the spirit and scope of the invention and the invention is to be limited only by the following claims:

What is claimed is:

1. A light delivery catheter comprising:
   a proximal shaft having first and second lumens extending therethrough;
   a distal shaft having a single lumen extending therethrough;
   a short tapered section interconnecting the proximal and distal shafts;
   said first and second lumens being adapted to receive a guidewire and a light guide respectively,
   said single lumen being aligned with said first and second lumens to permit either the guidewire in said first lumen or the light guide in said second lumen to extend into said single lumen in the distal shaft; and
   a hub at the proximal end of said proximal shaft, said hub having at least three ports, a first port connected to the first lumen through which the guidewire may enter the lumen, a second port connected to the second lumen through which the light guide may enter the second lumen, and a third port connected to one of the first and second lumens through which a fluid may be applied to the lumen to which the third port is connected.

2. A catheter as claimed in claim 1 wherein the third port is connected to apply a fluid to the first lumen and including a fourth port connected to said second lumen through which a contrast fluid may be applied to the lumen.

3. A catheter as claimed in claim 2 wherein the first and second ports are hemostatic valves and wherein the third and fourth ports are Leur connectors.

4. A catheter as claimed in claim 3 including a check valve on each of said Leur connectors.

5. A method for removing a blood clot in a patient's blood vessel including the steps of:
   (a) advance a guidewire and a catheter mounted thereon from an entry point on the patient to and through said clot;
   (b) remove the guidewire from at least the distal end of said catheter and advance a light guide to said distal end;
   (c) flow a contrast fluid through said catheter and out the distal end thereof;
   (d) apply light energy through the light guide; and
   (e) slowly pull the catheter back through the clot as the clot is lysed by the laser.

6. A method as claimed in claim 5 including the step of utilizing at least one of acoustic feedback from a unique sound produced during lysing of the clot and optical feedback from an image of the clot being lysed to control the rate at which the catheter is pulled back during step (e).

7. A method as claimed in claim 5 including the steps performed after step (e) of
   (f) determine if the clot has been sufficiently lysed;
   (g) if the clot has not been sufficiently lysed, re-advance the catheter through the clot, advance the light guide to said distal end, and repeat steps (c), (d), and (e).

8. A method as claimed in claim 7 wherein step (g) includes the step performed before said readvance step of replace the light guide at the distal end of said catheter with said guidewire, and wherein said advance step of step (g) includes the step of replace the guidewire with the light guide at said distal end.

9. A method as claimed in claim 5 wherein said blood vessel is in the patient's brain.

* * * * *